(12) United States Patent
Kishore et al.

(10) Patent No.: US 11,857,775 B2
(45) Date of Patent: Jan. 2, 2024

(54) FLUID FLOW SYSTEM FOR BUBBLE AND FLUID DETECTION

(71) Applicant: Honeywell International Inc., Charlotte, NC (US)

(72) Inventors: Kuna V S R Kishore, Bangalore (IN); Abhishek Joshi, Bangalore (IN); Kumaran S Narasimhan, Bangalore (IN); Kaligaselvi Lenin, Bangalore (IN); Manjunatha Hm, Bangalore (IN); Varun Thakurta, Bangalore (IN); Sudheer Beligere Sreeramu, Bangalore (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 146 days.

(21) Appl. No.: 17/444,620

(22) Filed: Aug. 6, 2021

(65) Prior Publication Data

US 2022/0409825 A1 Dec. 29, 2022

(30) Foreign Application Priority Data

Jun. 23, 2021 (IN) .............................. 202111028143

(51) Int. Cl.
*A61M 5/36* (2006.01)
*G01N 29/032* (2006.01)
(52) U.S. Cl.
CPC ............ *A61M 5/365* (2013.01); *G01N 29/032* (2013.01); *G01N 2291/02433* (2013.01)
(58) Field of Classification Search
CPC ........ A61M 5/365; A61M 2005/16863; A61M 5/16854; A61M 2205/3375; G01N 29/032; G01N 2291/02433; G01N 2291/048
See application file for complete search history.

(56) References Cited

U.S. PATENT DOCUMENTS

| 6,629,449 | B1 | 10/2003 | Kline-Schoder et al. |
| 9,743,909 | B1 | 8/2017 | Sapozhnikov et al. |

(Continued)

FOREIGN PATENT DOCUMENTS

WO    2020/072234 A1    4/2020

OTHER PUBLICATIONS

European search report dated Mar. 3, 2022 for EP Application No. 21195550.

*Primary Examiner* — Peter J Macchiarolo
*Assistant Examiner* — John M Royston
(74) *Attorney, Agent, or Firm* — ALSTON & BIRD LLP

(57) ABSTRACT

A fluid flow system and a method for detecting air bubble and liquid are provided. The fluid flow system comprises a force sensor configured to monitor at least one of an air bubble or an occlusion in a flow tube. The fluid flow system comprises a controller to execute the method. The controller is configured to monitor an output signal of a force sensor of the fluid flow system, and the output signal comprises an Alternating Current (AC) component and a Direct Current (DC) component, and detect a change in the output signal to a new output signal based on a number of transitions to the new output signal, and a time duration of the new output signal. The controller compares the change in the output signal with one of a predefined number of transitions or a predefined time and determines a new threshold when the change in the output signal exceeds one of the predefined number of transitions or the predefined time.

20 Claims, 9 Drawing Sheets

(56) References Cited

U.S. PATENT DOCUMENTS

| | | | |
|---|---|---|---|
| 2008/0184784 A1* | 8/2008 | Dam | G01N 29/222 |
| | | | 73/632 |
| 2009/0078047 A1* | 3/2009 | Dam | A61M 1/3639 |
| | | | 73/606 |
| 2012/0312072 A1 | 12/2012 | Stringham et al. | |
| 2018/0165422 A1* | 6/2018 | Mirov | G01K 13/02 |
| 2020/0096405 A1* | 3/2020 | Wan | G01L 1/26 |
| 2020/0353166 A1 | 11/2020 | Brown et al. | |

* cited by examiner

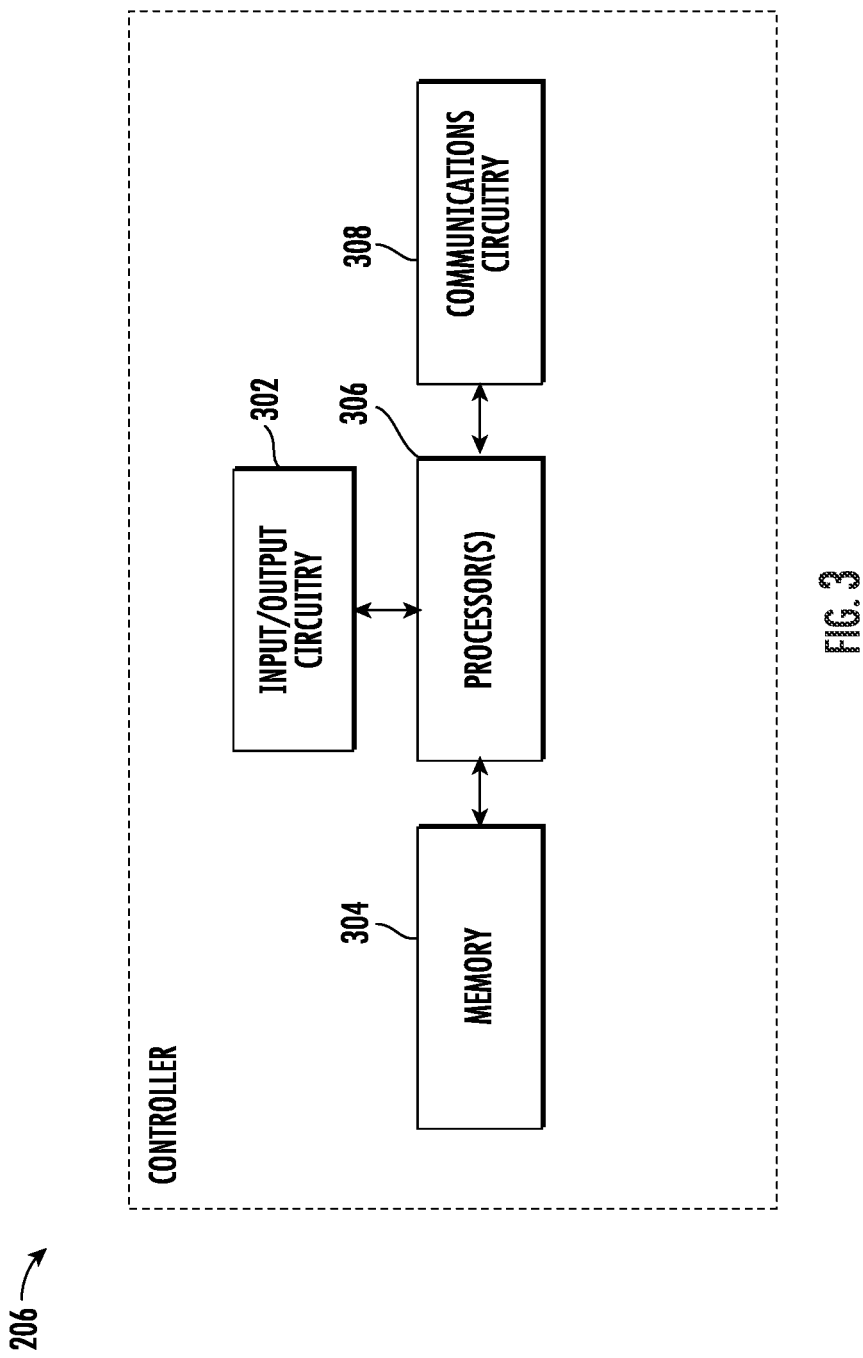

TIME (ms)

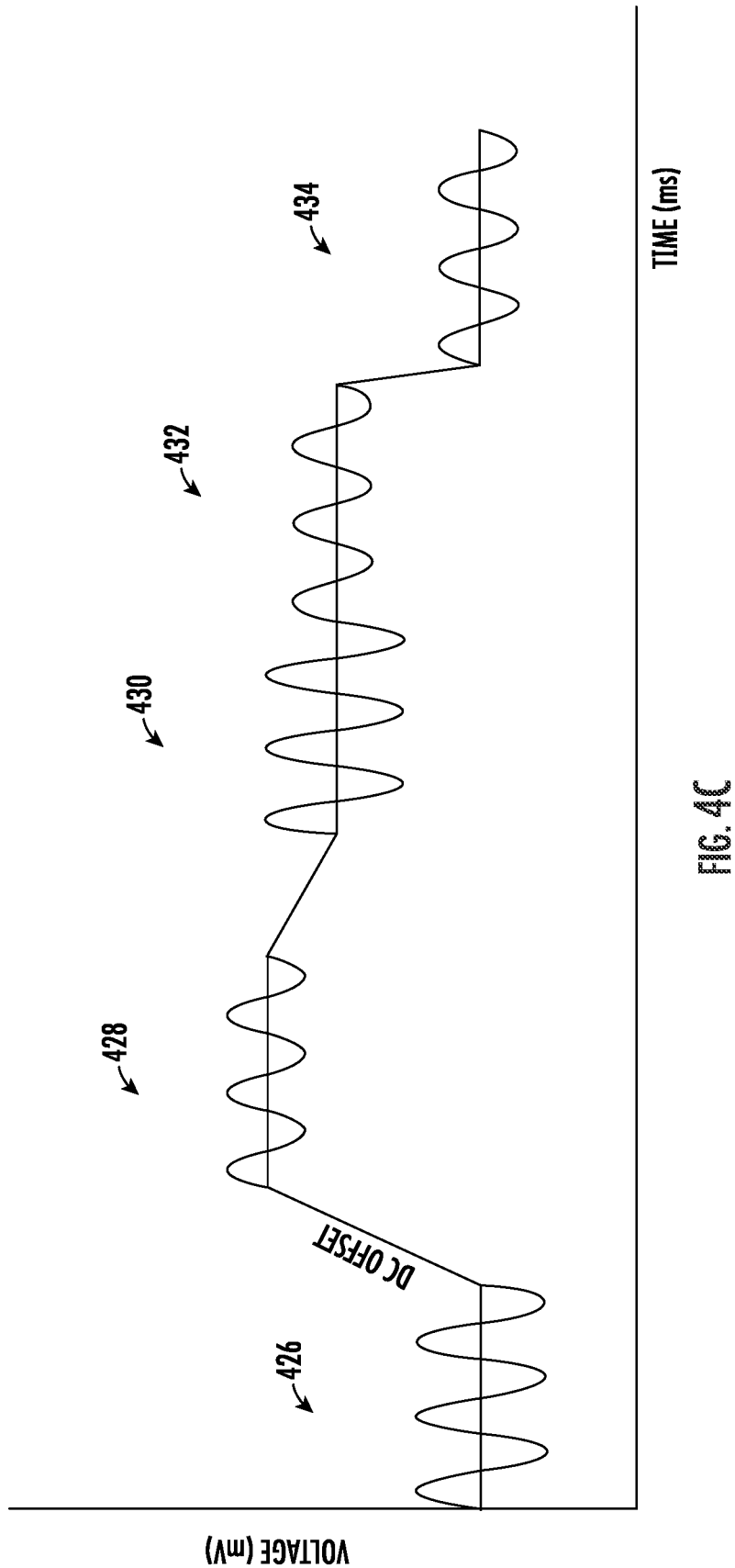

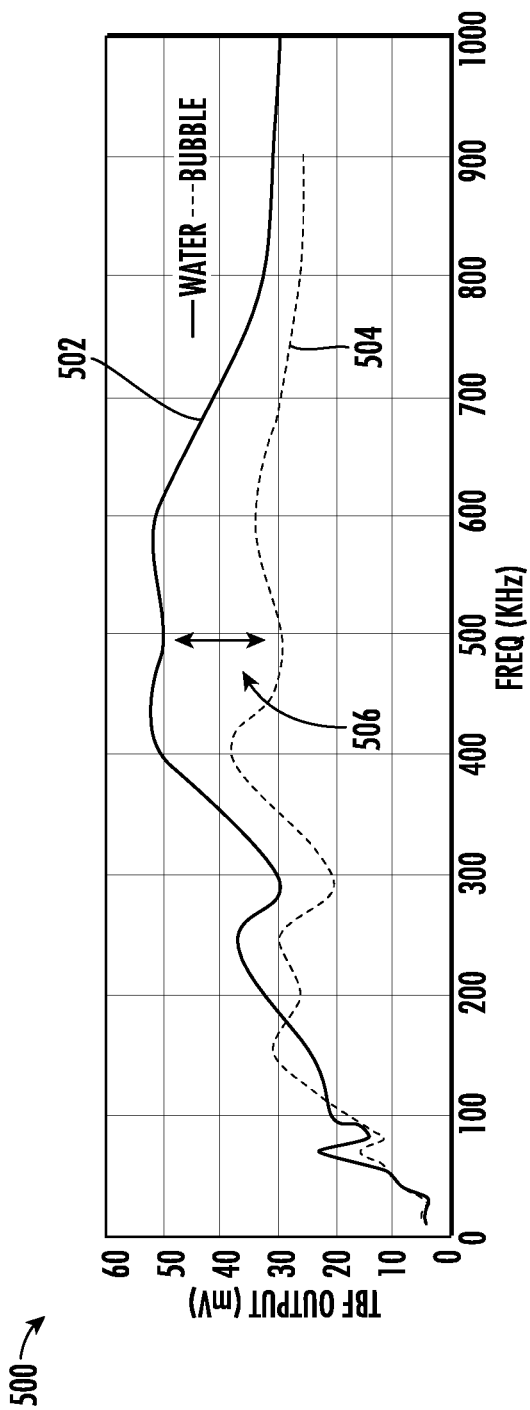

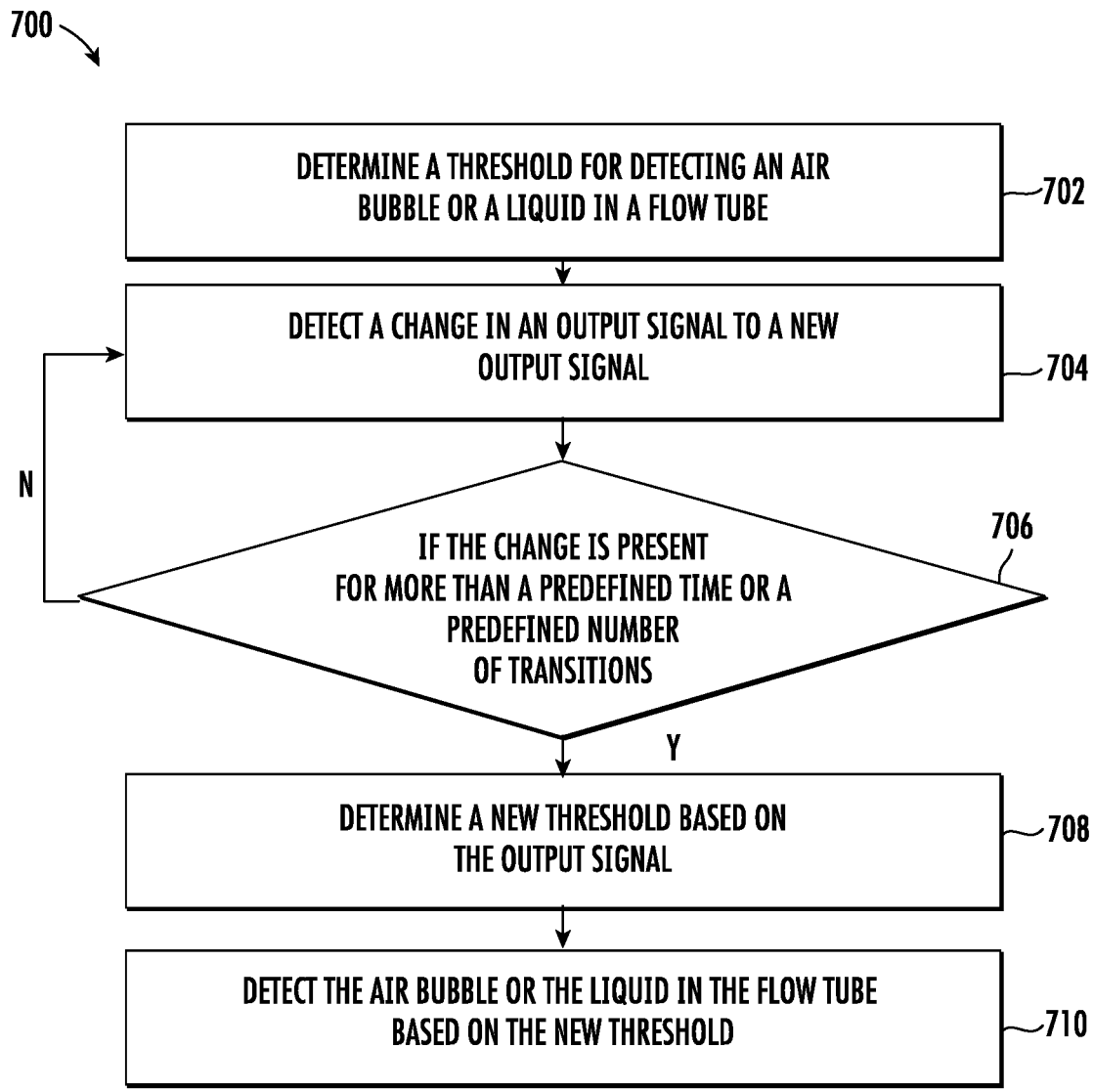

FLUID FLOW SYSTEM FOR BUBBLE AND FLUID DETECTION

CROSS-REFERENCE TO RELATED APPLICATIONS

This application claims priority to and the benefit of foreign Indian Provisional Patent Application Serial No. 202111028143, filed on Jun. 23, 2021 with the Government of India Patent Office and entitled "Fluid Flow System For Bubble And Fluid Detection," each of which is incorporated herein by reference in its entirety.

TECHNOLOGICAL FIELD

Example embodiments of the present disclosure relate generally to fluid flow systems, and more particularly, to a fluid flow system for detecting bubbles and liquid in an Intravenous (IV) tube.

BACKGROUND

Fluid flow systems may be used in a multitude of applications in order to transport or otherwise move fluids from one location to another. In particular, the fluid flow systems may be incorporated as components of safety measures associated with intravenous infusions, a treatment measure in the daily routine of modern hospitals. Such fluid flow systems generally comprise an intravenous infusion device, such as a cannula or a catheter, for infusion of fluids, such as nutrients, blood and medication to a patient, one or more fluid sources for containing an intravenous fluid or a component thereof, and a fluid line assembly having an Intravenous (IV) tube providing fluid communication between the intravenous infusion device and the one or more fluid sources.

The fluid flow systems also include one or more sensors, such as fluid sensors to measure a precise amount of a fluid being delivered to the patient. The fluid flow systems may also comprise other sensors such as pressure sensors to detect fluid line blockage and ultrasonic sensors to detect air bubbles present in the IV tube.

BRIEF SUMMARY

The illustrative embodiments of the present disclosure relate to a method for detecting an air bubble or liquid in a flow tube of a fluid flow system. The method comprises monitoring a first output signal of a force sensor of the fluid flow system for a change from the first output signal to a second output signal. The change from the first output signal to the second output signal comprises one of a change in amplitude of an Alternating Current (AC) component of the first output signal and a change in a signal level of a Direct Current (DC) component of the first output signal. Further, the method comprises detecting the change from the first output signal to the second output signal. The change in the amplitude of the AC component is detected based on an increase or a decrease of the amplitude of the AC component, and the change in the signal level of the DC component is detected based on a shift of the signal level from a first signal level to a second signal level. Further, the method comprises determining one of a time duration of the second output signal of the force sensor from an instance the first output signal is changed to the second output signal, and a number of transitions in consecutive signal levels of the DC component from the first signal level to the second signal level, and comparing the time duration of the second output signal with a predefined time and the number of transitions with a predefined number of transitions. The method comprises determining a threshold when one of the time duration of the second output signal exceeds the predefined time, and the number of transitions of the DC component exceeds a predefined number of transitions, wherein the threshold is determined based on a predefined percentage of the second output signal.

In an example embodiment, the shift of the DC component from the first signal level to the second signal level comprises one of a change from a low signal level to a high signal level and a change from a high signal level to a low signal level.

In an example embodiment, the first output signal is received in response to ultrasonic signals transmitted at a frequency range of 20 Kilo Hertz (KHz) to 1 Mega Hertz (MHz).

In an example embodiment, the flow tube is disposed within a channel of the force sensor with a tube compression of 10-40% of a diameter of the flow tube.

In an example embodiment, the method further comprises detecting the air bubble or liquid in the flow tube based on the threshold.

In an example embodiment, the predefined percentage is 65% of the second output signal.

In an example embodiment, the change from the first output signal to the second output signal is in response to one or more of an uncontrolled sensor position of the force sensor, or movement of the flow tube or change in flow rate or pressure.

In an example embodiment, a fluid flow system is disclosed. The fluid flow system comprises a force sensor configured to monitor at least one of an air bubble or an occlusion in a flow tube, the force sensor configured to receive ultrasonic signals from an ultrasonic transducer, the ultrasonic transducer having an emitting face configured to emit the ultrasonic signals, and the emitting face is configured to face the flow tube. The fluid flow system comprises a controller, electrically coupled with the force sensor, wherein the controller is configured to monitor a first output signal of a force sensor of the fluid flow system for a change from the first output signal to a second output signal, wherein the change from the first output signal to the second output signal comprises at least one of a change in amplitude of an Alternating Current (AC) component of the first output signal and a change in a signal level of a Direct Current (DC) component of the first output signal. The controller is further configured to detect the change from the first output signal to the second output signal, wherein the change in the amplitude of the AC component is detected based on an increase or a decrease of the amplitude of the AC component, and the change in the signal level of the DC component is detected based on a shift of the signal level from a first signal level to a second signal level. The controller is configured to determine one of a time duration of the second output signal of the force sensor, and a number of transitions in consecutive signal levels of the DC component from the first signal level to the second signal level, and compare the time duration of the second output signal with a predefined time and the number of transitions with a predefined number of transitions. The controller is configured to determine a threshold when one of the time duration of the second output signal exceeds the predefined time, and the number of transitions of the DC component exceeds a predefined number of transitions, wherein the threshold is determined based on a predefined percentage of the second output signal.

In some embodiments, the force sensor has a receiving face configured to receive the ultrasonic signals for detecting a change in amplitude of the ultrasonic signals, and the ultrasonic signals propagate through the flow tube prior to receiving by the force sensor.

In an example embodiment, the first output signal is received in response to ultrasonic signals transmitted at a frequency range of 20 Kilo Hertz (KHz) to 1 Mega Hertz (MHz).

In some embodiments, the flow tube is disposed within a channel of the force sensor with a tube compression of 10-40% of a diameter of the flow tube.

In an example embodiment, the controller is configured to detect the air bubble or liquid in the flow tube based on the threshold.

In an example embodiment, the predefined percentage is 65% of the second output signal.

In an example embodiment, the change from the first output signal to the second output signal is in response to one or more of an uncontrolled sensor position, or movement of the flow tube or change in flow rate or pressure.

In some embodiments, the controller is configured to detect the shift of the DC component from the first signal level to the second signal level based on one of a change from a low signal level to a high signal level and a change from a high signal level to a low signal level.

In an example embodiment, a non-transitory computer-readable medium storing instructions for detecting an air bubble or liquid in a flow tube of a system is disclosed. The instructions, when executed, cause the system to monitor a first output signal of a force sensor of the system for a change from the first output signal to a second output signal. The change from the first output signal to the second output signal comprises at least one of a change in amplitude of an Alternating Current (AC) component of the first output signal and a change in a signal level of a Direct Current (DC) component of the first output signal. Further, the instructions when executed cause the system to detect the change from the first output signal to the second output signal, and the change in the amplitude of the AC component is detected based on an increase or a decrease of the amplitude of the AC component, and the change in the signal level of the DC component is detected based on a shift of the signal level from a first signal level to a second signal level. The instructions cause the system to determine one of a time duration of the second output signal of the force sensor, and a number of transitions in consecutive signal levels of the DC component from the first signal level to the second signal level and compare the time duration of the second output signal with a predefined time and the number of transitions with a predefined number of transitions. The instructions cause the system to determine a threshold when one of the time duration of the second output signal exceeds the predefined time, and the number of transitions of the DC component exceeds a predefined number of transitions, wherein the threshold is determined based on a predefined percentage of the second output signal.

In some embodiments, the non-transitory computer readable medium stores instructions for detecting the air bubble or liquid in the flow tube based on the threshold.

In an example embodiment, the predefined percentage is 65% of the second output signal.

In some embodiments, the change from the first output signal to the second output signal is in response to one or more of an uncontrolled sensor position, or movement of the flow tube or change in flow rate or pressure.

In an example embodiment, the non-transitory computer-readable medium storing instructions to detect the shift of the DC component from the first signal level to the second signal level based on one of a change from a low signal level to a high signal level and a change from a high signal level to a low signal level.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIG. 3 illustrates a schematic block diagram of example circuitry that may perform various operations, in accordance with an example embodiment of the present disclosure;

FIGS. 4A, 4B and 4C are graphical representations of a response of a force sensor, in accordance with an example embodiment of the present disclosure;

FIG. 5 is a graphical representation of a sensitivity of a force sensor, in accordance with an example embodiment of the present disclosure;

FIG. 7 illustrates an example flow chart for a method for detecting an air bubble or liquid in a flow tube of a fluid flow system, in accordance with an example embodiment of the present disclosure;

DETAILED DESCRIPTION

Figures 1A, 1B:
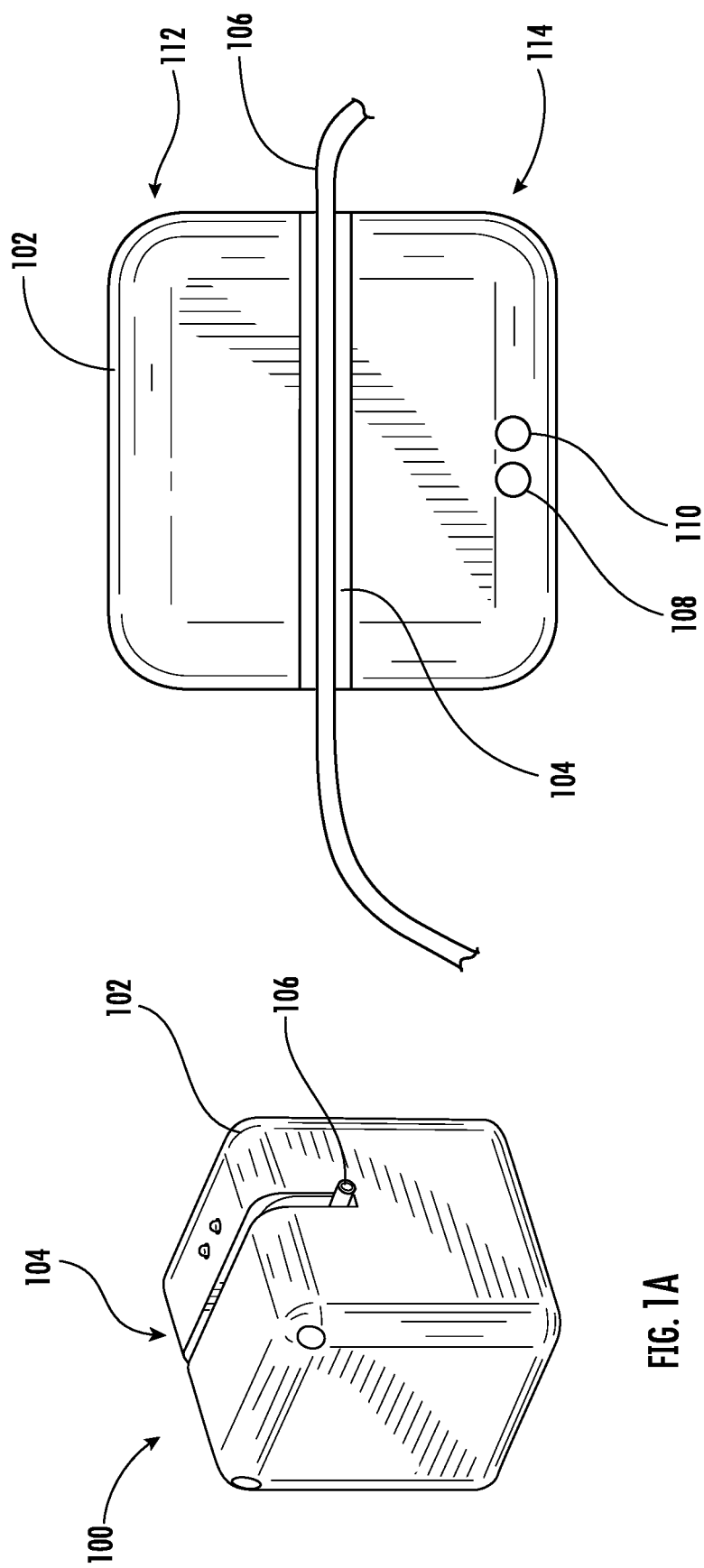
FIGS. 1A and 1B illustrate a perspective view and a top view of a fluid sensor respectively, in accordance with an example embodiment of the present disclosure.

Some embodiments of the present disclosure will now be described more fully hereinafter with reference to the accompanying drawings, in which some, but not all embodiments are shown. Indeed, the disclosure may be embodied in many different forms and should not be construed as limited to the embodiments set forth herein; rather, these embodiments are provided so that this disclosure will satisfy applicable legal requirements. The terms "or" and "optionally" are used herein in both the alternative and conjunctive sense, unless otherwise indicated. The terms "illustrative" and "exemplary" are used to be examples with no indication of quality level. Like numbers refer to like elements throughout.

As used herein, the term "controller" refers to any user device, computing device, object, or system which may be in network communication with the first temperature sensor, the second temperature sensor, and/or the heating element. For example, the controller may refer to a wireless electronic device configured to perform various temperature related operations in response to temperature data generated by the first temperature sensor and/or the second temperature sensor. The controller may be configured to communicate with the first temperature sensor, the second temperature sensor, the heating element, and/or the like via Bluetooth, NFC, Wi-Fi, 3G, 4G, 5G protocols, and the like. In some instances, the controller may comprise the first temperature sensor, the second temperature sensor, and/or the heating element.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Having set forth a series of definitions called-upon throughout this application, an example system architecture and example apparatus is described below for implementing example embodiments and features of the present disclosure.

Fluid flow systems have fluid sensors to detect air bubbles and debris in Intravenous (IV) tubes by monitoring various parameters, such as pressure, rate of flow of fluids through an IV tube, and amplitude of signal response of a fluid sensor. The fluid sensor detects air bubbles and debris in an IV tube based on radiations emitted by a transmitter of the fluid sensor that propagates through the IV tube and are received by a receiver of the fluid sensor. Existing fluid sensors use high frequency ultrasonic acoustic waves within a range of 1.7 Megahertz (MHz) to 5 MHz using a piezo electric transducer. Such high frequency ultrasonic waves are received and detected by another piezoelectric transducer. The high frequency range is typically used to detect liquid and bubbles in the IV tube. However, not all types of fluid sensors are compatible with such a high frequency range operation. For instance, fluid sensors that use other type of sensors, such as force sensors or pressure sensors with the ultrasonic transducers are not operable with the high frequency range and may have issues regarding operation and accuracy of detection. An optimum frequency range is required for the fluid sensors to operate and achieve a desired efficiency and accuracy of detection of air bubbles and liquid.

The IV tube is in surface contact with the fluid sensor with the IV tube pressed against the transmitter and the receiver of the fluid sensor for detection of the radiations. The IV tube may have subtle movements during patient administration, and the surface contact or contact area of the IV tube with the transmitter and the receiver varies causing unwanted variations in amplitude of radiations detected by the receiver and a corresponding output signal. The variations in surface contact or tube contact pressure and area affects the frequency of the ultrasonic signals and response of the force sensor. A poor coupling between the IV tube and the fluid flow sensor results in an insufficient amount of ultrasonic signals propagating through the IV tube and causing improper and inaccurate detection of air bubbles and liquid.

Further, in an event of occlusion, the pressure inside the IV tube increases, and the surface of the IV tube becomes stiffer. The change in stiffness of the surface also affects the radiations and the corresponding output signal, as more radiations of higher amplitude are required to propagate through the IV tube to reach the receiver, when the surface is stiffer. This results in erroneous signal detection. For transmitting the ultrasonic signals that propagate through the IV tube, a sufficient level of pressure of the ultrasonic signals is required for uninterrupted detection of air bubbles and liquid.

Various example embodiments described in present disclosure relates to a fluid flow system for monitoring delivery of fluids to patients with improved detection of air bubbles and liquid in an IV tube or a flow tube. The fluid flow system has a force sensor that holds the IV tube or the flow tube and monitors the flow tube for various parameters such as flow rate, and pressure, air bubbles and liquid. The force sensor receives ultrasonic signals from the ultrasonic transducer. The fluid flow system has a controller connected to the force sensor. The controller detects an output signal from the force sensor and detects air bubbles or liquid based on the output signal.

In an example, the output signal has two components, an Alternating Current (AC) component and a Direct Current (DC) component. An advantage of using such an output signal having both the AC component and the DC component is to receive information about the air bubbles and occlusion from the same signal, thereby preventing use of different or separate signals for each air bubbles and occlusion detection.

In an example, the controller detects a change in the output signal from a first output signal to a second output signal, for instance, in response to an uncontrolled sensor position, or movement of the flow tube or change in flow rate or pressure of the liquid in the flow tube. The controller determines a time duration time duration of the second output signal of the force sensor from an instance the first output signal is changed to the second output signal. The controller determines a number of transitions in consecutive signal levels of the DC component from a first signal level to a second signal level. Further, the controller compares the time duration with a predefined time, and the number of transitions with a predefined number of transitions.

After comparing, the controller determines a threshold, also referred to as a new threshold herein, for detecting the air bubbles or liquid. The controller then detects the air bubble and the liquid based on the threshold. For instance, when there is a change in the second output signal to a third output signal less than the threshold, an air bubble is detected by the controller. In this manner, the threshold for the fluid flow system is dynamically updated based on the change in the output signal in response to various factors, such as uncontrolled sensor position, or movement of the flow tube or change in flow rate or pressure and other conditions. Thus, the disclosed fluid flow system is robust and accurate in detecting the air bubbles when conditions of the flow tube and the sensor change thereby enhancing reliability of the fluid flow system.

In an example, the force sensor is operated at a frequency range of 20 Kilo Hertz (KHz) to 1 Mega Hertz (MHz). The force sensor operated in such a frequency range provides efficient and accurate detection of the air bubbles and the liquid with clear distinction between bubble detection and liquid detection. In an example, the flow tube is disposed within a channel of the force sensor with a tube compression of 10-40% of a diameter of the flow tube to achieve better coupling efficiency. The ultrasonic signals are transmitted with a sufficient Acoustic Power Level (APL) for improved and continuous propagation of the signals through the flow tube.

The details regarding components of the fluid flow system and their working is described in detail with reference to subsequent figures.

The components illustrated in the figures represent components that may or may not be present in various example embodiments described herein such that embodiments may include fewer or more components than those shown in the figures while not departing from the scope of the disclosure.

Turning now to the drawings, the detailed description set forth below in connection with the appended drawings is intended as a description of various example configurations and is not intended to represent the only configurations in which the concepts described herein may be practiced. The detailed description includes specific details for the purpose of providing a thorough understanding of various concepts with like numerals denoting like components throughout the several views. However, it will be apparent to those skilled in the art of the present disclosure that these concepts may be practiced without these specific details.

FIGS. 1A and 1B illustrate perspective and top views of a fluid sensor 100 of a fluid flow system, in accordance with an example embodiment of the present disclosure. As shown, the fluid sensor 100 has an outer body or a housing 102 defining a channel 104 to hold a flow tube 106. The fluid sensor 100 also comprises multiple indicators, such as indicators 108 and 110 on a top face of the housing 102. In an example, the housing 102 defines an exterior of the fluid sensor 100 and may have a height, length, and a width, wherein the length of the housing 102 is defined by a distance between a first end and a second end. The housing 102 defines a shape of the fluid sensor 100. For instance, the housing is a cube shown in the figure. The housing 102 can also have other shapes to fit into the fluid flow system.

The channel 104 is defined on the top face of the housing 102 and has a predefined width to receive the flow tube 106. As shown, the channel 104 is defined along a center region of the top face of the housing 102. The channel 104 divides the top face of the housing 102 into two parts, a first portion 112 and a second portion 114. Each of the first portion 112 and the second portion 114 houses a sensor as described in more detail with reference to subsequent figures. In various embodiments, the flow tube 106 has a length, and a diameter, and comprises an outer circumferential wall, an inner circumferential wall, and a wall thickness extending between the outer circumferential wall and the inner circumferential wall. In an example, the flow tube 106 defines an interior channel within the inner wall configured to direct the flow of fluid from one location to another location.

The flow tube 106 may comprise a resilient material, for e.g., a silicone material, a polyvinyl chloride material, and/or the like. In an example, the indicators 108 and 110 glow with different colors to signal when a bubble is detected or a flow occlusion event is detected. For instance, the indicator 108 glowing with a red color indicates a bubble detected and the indicator 110 glowing with a red color indicates detection of the flow occlusion event. These signals for air bubble and flow occlusion are electrically communicated to a controller of the fluid flow system for control action as required by the fluid flow system.

Figure 2:
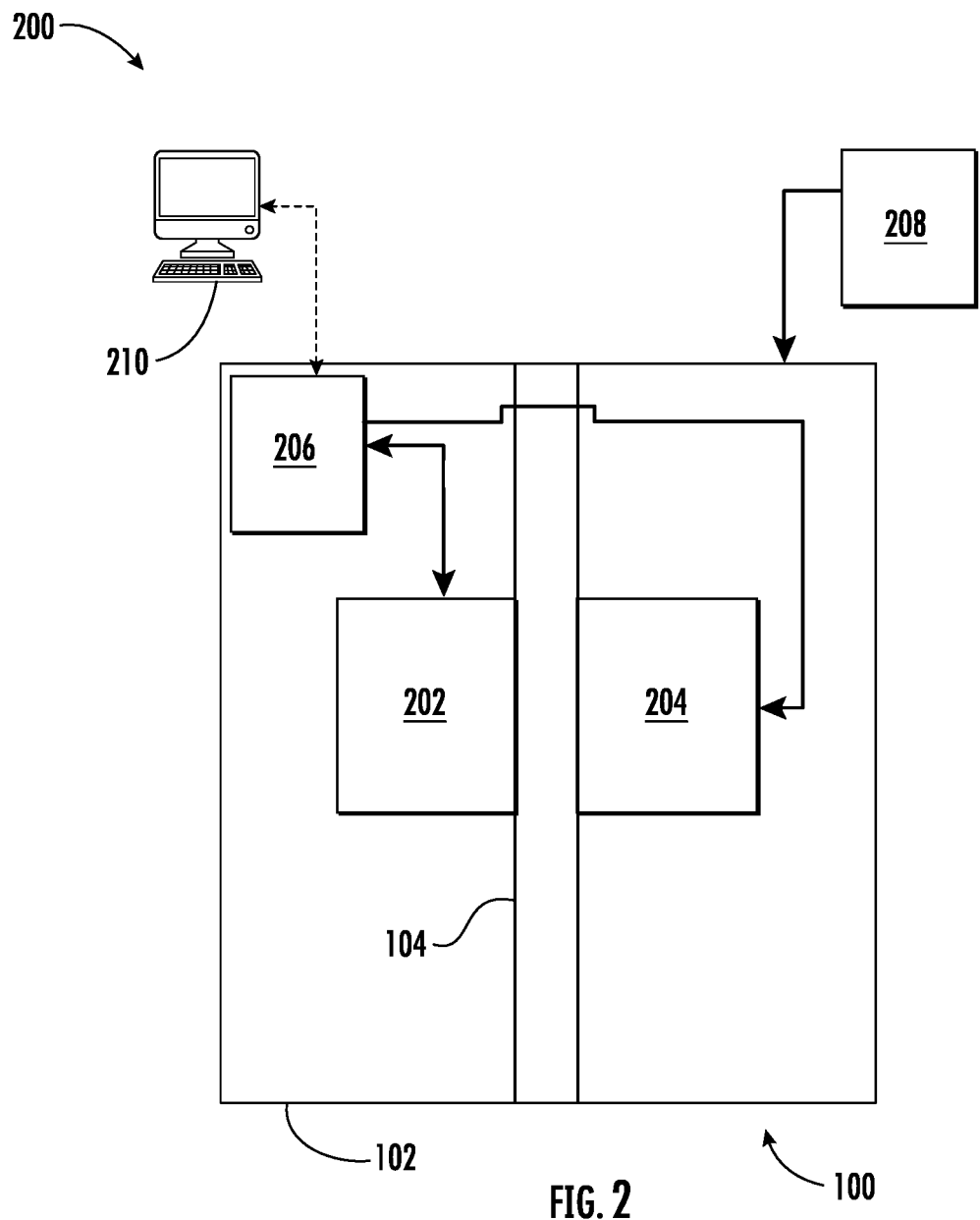
FIG. 2 illustrates a fluid flow system with a controller, in accordance with an example embodiment of the present disclosure.

FIG. 2 illustrates a fluid flow system 200, in accordance with an example embodiment of the present disclosure. The fluid flow system 200 comprises an ultrasonic transducer 202, a force sensor 204 and a controller 206. The controller 206 is coupled to the ultrasonic transducer 202 and the force sensor 204. Further, the fluid flow system 200 comprises a power supply 208 and a server or a computer 210.

As shown, the housing 102 comprises the channel 104 extending from the first end of the housing 102 to the second end and configured to receive and secure a portion of the flow tube 106. The housing 102 may be configured to enclose both the ultrasonic transducer 202 and the force sensor 204 within the interior portion of the housing 102. The ultrasonic transducer 202 and the force sensor 204 are each coupled to an interior portion of the housing 102 and are spaced apart within the interior portion of the housing 102 to define the channel 104 between the two sensors. The ultrasonic transducer 202 and the force sensor 204 of the illustrated embodiment are aligned within the housing 102 so as to face one another, that is, an emitting face of the ultrasonic transducer 202 is facing towards a receiving face of the force sensor 204 such that waves or signals generated by the ultrasonic transducer 202 and emitted from the emitting face of the ultrasonic transducer 202 travel towards the receiving face of the force sensor 204. In such an exemplary configuration, the ultrasonic transducer 202 and the force sensor 204 are arranged to face a direction perpendicular to the length of the channel 104, and may define at least a portion of the channel 104.

The power supply 208 is configured to receive power and power the fluid sensor 100. In an example, the power supply 208 may comprise one or more batteries, one or more capacitors, one or more constant power supplies, e.g., a wall-outlet, and/or the like. In an example, the power supply 208 may comprise an external power supply positioned outside the housing 102 and configured to deliver alternating or direct current power to the fluid sensor 100. In another example, the power supply 208 may comprise an internal power supply integrated within the fluid flow system, for example, one or more batteries, positioned within the housing 102, to obtain power from within the fluid flow system.

In various embodiments, power may be supplied to the controller 206 to enable distribution of power to the various components described herein. In some embodiments, each of the components of the fluid sensor 100 may be connected to controller 206 (e.g., for electronic communication), which may be configured to facilitate communication and functional control therebetween.

As illustrated in FIG. 3, the controller 206 may include an input/output circuitry 302, a memory 304, a processor 306, and communications circuitry 308. In an example embodiment, the controller 206 may include a communication module, an on-board display, and signal analysis circuitry (not shown in the figure). For example, the controller 206 may comprise a driving circuit and a signal processing circuit. In various embodiments, the controller 206 may be configured to power the force sensor 204 and/or receive an output signal from the force sensor 204. In various embodiments, the controller 206 may be configured to power the ultrasonic transducer 202 and transmit a drive signal to the ultrasonic transducer 202. In various embodiments, the controller 206 may be configured to transmit output signals out to external components via universal serial bus (USB) or any other wired connection. In various embodiments, an on-board display may be configured to display a variety of signals transmitted from or received by the controller 206. In various embodiments, the controller 206 may be embodied as a single chip (e.g., a single integrated-circuit chip) configured to provide power signals to both the ultrasonic transducer 202 and the force sensor 204, to receive and process the output signal from the force sensor 204, and/or to compensate for any detected changes in environmental factors such as, for example, temperature, flow, or pressure within the flow tube 106. In an example, the controller 206 is configured so as to enable wireless communication within a network to a variety of wirelessly enabled devices, e.g., a user mobile device, a server or a computer 210, and/or the like. The controller 206 may be configured to execute the operations described below in connection with FIGS. 4A and 4B. Although components 302-308 are described in some cases using functional language, it should be understood that the particular implementations necessarily include the use of particular hardware. It should also be understood that certain of these components 302-308 may include similar or common hardware. For example, two sets of circuitry may both leverage use of the same memory 304, the processor 306, and the communications circuitry 308, or the like to perform their associated functions, such that duplicate hardware is not required for each set of circuitry.

The use of the term "circuitry" as used herein includes particular hardware configured to perform the functions associated with respective circuitry described herein. As described in the example above, in some embodiments, various elements or components of the circuitry of the controller 206 may be housed within the fluid sensor 100. It will be understood in this regard that some of the components described in connection with the controller 206 may be housed within one or more of the device of FIG. 3, while other components are housed within another of these devices, or by yet another device not expressly illustrated in FIG. 3.

The term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the controller 206 may provide or supplement the functionality of particular circuitry.

In some embodiments, the processor 306 (and/or co-processor or any other processing circuitry assisting or otherwise associated with the processor 306) may be in communication with the memory 304 via a bus for passing information among components of the controller 206. The memory 304 may be non-transitory and may include, for example, one or more volatile and/or non-volatile memories. In other words, for example, the memory may be an electronic storage device (e.g., a non-transitory computer readable storage medium). The memory 304 may be configured to store information, data, content, applications, instructions, or the like, for enabling the controller 206 to carry out various functions in accordance with example embodiments of the present invention.

The processor 306 may be embodied in a number of different ways and may, for example, include one or more processing devices configured to perform independently. Additionally or alternatively, the processor 306 may include one or more processors configured in tandem via a bus to enable independent execution of instructions, pipelining, and/or multithreading. The use of the term "processing circuitry" may be understood to include a single core processor, a multi-core processor, multiple processors internal to the computing device, and/or remote or "cloud" processors.

In an example embodiment, the processor 306 may be configured to execute instructions stored in the memory 304 or otherwise accessible to the processor 306. Alternatively or additionally, the processor 306 may be configured to execute hard-coded functionality. As such, whether configured by hardware or by a combination of hardware with software, the processor 306 may represent an entity (e.g., physically embodied in circuitry) capable of performing operations according to an embodiment of the present invention while configured accordingly. Alternatively, as another example, when the processor 306 is embodied as an executor of software instructions, the instructions may specifically configure the processor 306 to perform the algorithms and/or operations described herein when the instructions are executed.

The controller 206 further includes input/output circuitry 302 that may, in turn, be in communication with processor 306 to provide output to a user and to receive input from a user, user device, or another source. In this regard, the input/output circuitry 302 may comprise a display that may be manipulated by a mobile application. In some embodiments, the input/output circuitry 302 may also include additional functionality including a keyboard, a mouse, a joystick, a touch screen, touch areas, soft keys, a microphone, a speaker, or other input/output mechanisms. The processor 306 and/or user interface circuitry comprising the processor 306 may be configured to control one or more functions of a display through computer program instructions (e.g., software and/or firmware) stored on a memory accessible to the processor 306 (e.g., memory 304, and/or the like).

The communications circuitry 308 may be any means such as a device or circuitry embodied in either hardware or a combination of hardware and software that is configured to receive and/or transmit data from/to a network and/or any other device, circuitry, or module in communication with the controller 206. In this regard, the communications circuitry 308 may include, for example, a network interface for enabling communications with a wired or wireless communication network. For example, the communications circuitry 308 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

In addition, computer program instructions and/or other type of code may be loaded onto a computer, processor or other programmable circuitry to produce a machine, such that the computer, processor other programmable circuitry that execute the code on the machine create the means for implementing the various functions, including those described in connection with the components of controller 206.

As described above and as will be appreciated based on this disclosure, embodiments of the present invention may be configured as sensors, methods, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Figure 4A:
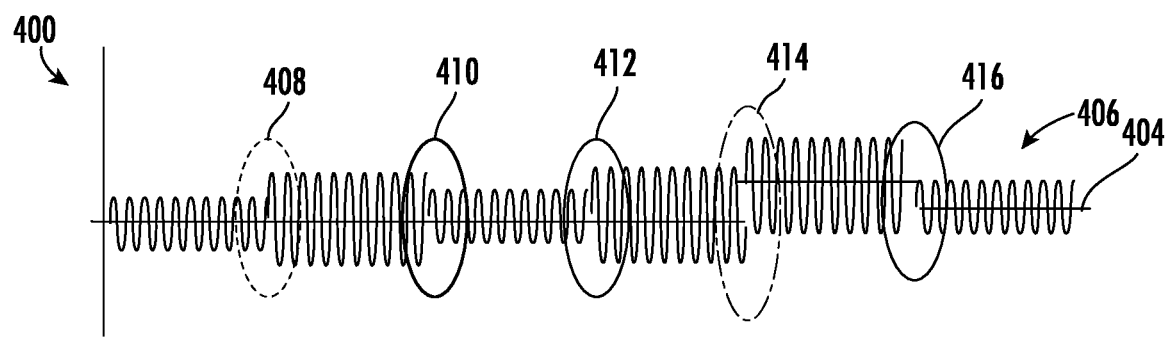
Figure 4B:
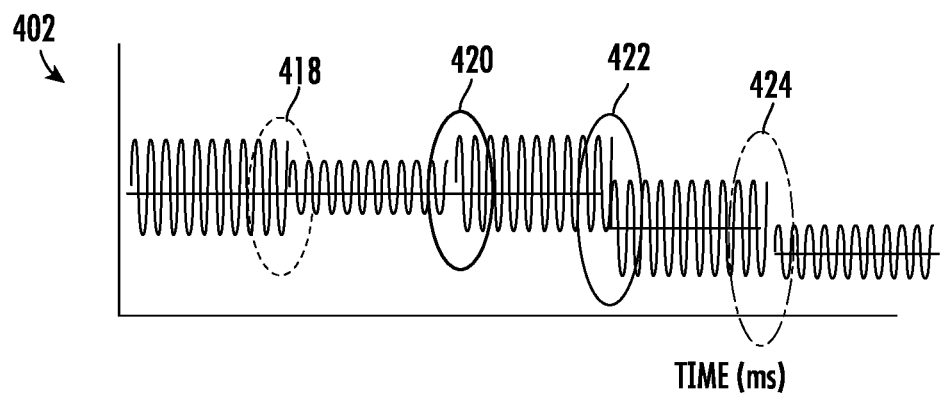

FIGS. 4A, 4B and 4C are graphical representations of a response of the force sensor 204, in accordance with an example embodiment of the present disclosure. The graphical representations 400 and 402 of FIGS. 4A and 4B show a force sensor output and time plotted on y-axis and x-axis respectively. The output signal wave has a Direct Current (DC) component, such as a base line component 404 and an Alternating Current (AC) component, such as amplitude 406. The controller 206 is configured to enable simultaneous monitoring of both the AC and DC components of the output signal for bubble and occlusion detection. Such a configuration may effectively reduce the error rate of the force sensor 204 by compensating for unwarranted external forces that may affect the sensor's acoustic baseline and lead in inaccuracies. Such a shift of the sensor's acoustic baseline may be caused by factors such as, for example, tubing/plastic deformation, and temperature change.

As shown in FIG. 4A, in an initial condition, there is no liquid inside the flow tube 106 and the flow tube 106 is filled with air. The ultrasonic transducer 202 transmits ultrasonic signals, and the ultrasonic signals are received by the force sensor 204 and detected by the controller 206. In an example, the ultrasonic transducer 202 transmits the ultrasonic signals at 80 Decibel (dB) at 10V drive at 290 KHz frequency. The base line component 404 and the amplitude 406 of the output signal detected by the controller 206 is as shown in the figure. The controller 206 computes an initial threshold for the initial condition. In an instance, when Intravenous (IV) administration is initiated, the flow tube 106 is filled with liquid and the output signal from the force sensor 204 changes from a first output signal to a second output signal. The transition 408 shows the change of the first output signal from the initial condition to the second output signal when the flow tube 106 has the liquid.

In an example, the controller 206 determines the change in an amplitude of the AC component of the output signal based on comparing the amplitude of the AC component of the second output signal with the amplitude of the AC component of the first output signal, and computing a difference between the amplitudes of the two AC components. The controller 206 then compares the difference with a predefined value and determines the change when the difference exceeds the predefined value. In a similar manner, the controller 206 detects a change in amplitude of the signal as shown in transitions 410 and 412. As shown in 410, the amplitude of the AC component of the second output signal decreases to a lower amplitude of a third output signal and in transition 412, the amplitude of the AC component of the third output signal increases to a higher amplitude of a fourth output signal. In transitions 414 and 416, the controller 206 detects a change in the signal levels of the DC component of the output signal. For instance, the controller 206 detects the signal level of the fourth output signal increases to a higher level in the transition 414 to a fifth output signal. The controller 206 measures the signal level of the fourth output signal and compares with the signal level of the fifth output signal to determine the difference between the signal level of the fourth output signal and the fifth output signal. In an example, the controller 206 determines a number of transitions in consecutive signal levels from the signal level of the fourth output signal to the signal level of the fifth output signal. In an embodiment, the controller 206 determines the time of the fifth output signal from an instance when the fourth output signal changes to fifth output signal. The controller 206 detects this change for every such transition in the output signal and compares the change with a predefined time or a predefined number of transition in consecutive signal levels to determine if the threshold is to be determined for a changed signal.

For example, in the initial condition, the output signal is at 7 millivolt (mV), and after the transition, the signal is at 10 mV. The controller 206 determines number of transitions of consecutive signal levels, for instance, from 7 mV to 8 mV, from 8 mV to 9 mV and from 9 mV to 10 mV. In another example, the controller 206 determines the total time duration for which the signal remains at a new level for instance at the second output signal when the first output signal changes to the second output signal. For example, the second output signal is present for about 1 second. Thereafter, the controller 206 compares the number of transitions, such as 3, with a predefined number of transitions, for instance, 2 or 3. The controller 206 compares the total time duration of 1 second with a predefined time, for instance, 0.5-1 second. When the number of transitions exceeds or equals the predefined number of transitions or the predefined time, such as in this example, the controller 206 recalculates the threshold based on the second output signal.

In an example, the controller 206 calculates the threshold based on a predefined percentage, such as 65% of the output signal after the transition or the change, for instance, the second output signal. For example, if the second output signal is at 10 mV, the controller 206 calculates the threshold as 65% of 10 mV, i.e. 6.5 mV. The controller 206 utilizes the threshold for detecting the air bubbles and liquid during operation of the force sensor 204. The threshold is calculated to accommodate prevailing tube conditions, such as changed sensor position, change in flow rate or pressure, or change in tube compression. The controller 206 reliably and accurately detects the state change and direction of state change (from high to low or low to high) of the output signal.

In an example, when the flow tube 106 has a flow occlusion, the DC component of the signal changes and there is no change in the AC component. In such an instance, the controller 206 may not determine a new threshold. However, when there is a drop in the flow occlusion, the DC component decreases, and the AC component is maintained at a level for the liquid. In such a scenario, if AC component also decreases then such a change is detected as a state change for the signal for detecting presence of air bubbles. In another instance, when the AC component increases, the controller 206 determines the new threshold.

In another example embodiment, in the initial condition, there is liquid inside the flow tube 106. Upon powering the fluid flow system 200, the initial threshold for bubble detection is calculated by the controller 206 based on the predefined percentage of the output signal in the initial condition. The flow tube 106 is continuously monitored by the controller 206 for possible signal level changes, as shown in transition 418 of FIG. 4B, for detecting presence of the air bubble based on the predefined percentage of 65% of the output signal. When the signal for bubble detection ends, the amplitude of AC component increases (state changes) and reaches a new level, shown in transition 420.

At this point, the controller 206 recalculates the threshold to accommodate prevailing tube conditions. In an example, when the flow tube 106 has flow occlusion with a low pressure in the flow tube 106, the signal level of the DC component decreases from a high signal level to a low signal level (as shown in transition 422) without any change in the AC component. In an example, if there is an increase in the AC component, the controller 206 recalculates the threshold to accommodate new tube conditions. In another example, if there is a decrease in the AC component (shown in transition 424), a bubble event is detected by the controller 206. If the flow pressure in the flow tube 106 decreases and air bubble is present, the air bubbles are detected based on the threshold calculated for the previous transition.

As shown in FIG. 4C, a region 426 of the output signal shows a condition, when there is no bubble or occlusion in the flow tube 106. In an event of presence of air bubble and full occlusion, the DC component of the signal rises to a new level shown in a region 428. In this region 428, the AC component of the signal decreases. In another condition, when there are no air bubbles and partial occlusion, the signal changes from the region 428 to a region 430. In the region 430, the DC component of the signal changes and the amplitude of the signal also varies.

In another condition, when there are air bubbles and partial occlusion present in the flow tube 106 (shown in region 432), the DC component of the signal remains constant and there is a slight variation in the amplitude of the signal. Thereafter, in a condition, when there is no bubble and no occlusion, the DC component of the signal falls to a lower level, as shown in a region 434.

FIG. 5 illustrates a graphical representation 500 of a sensitivity of the force sensor 204, in accordance with an example embodiment of the present disclosure. The graphical representation 500 show a force sensor output and frequency plotted on y-axis and x-axis respectively. The force sensor output has two signals, a signal 502 corresponding to presence of liquid within the flow tube 106 and a signal 504 corresponding to presence of air bubbles inside the flow tube 106. As shown in the figure, the difference 506 between the signals 502 and 504 is visible on the graphical representation 500 for the frequency range of 20 Kilo Hertz (KHz) to 1 Mega Hertz (MHz). In an example, at 500 KHz of frequency, the difference 506 between the signals 502 and 504 is maximum. Thus, the frequency range 20 KHz to 1 MHz provides an optimum frequency for the fluid flow system 200 to operate and distinctively detect bubbles and liquid in the flow tube 106.

Figure 6A:
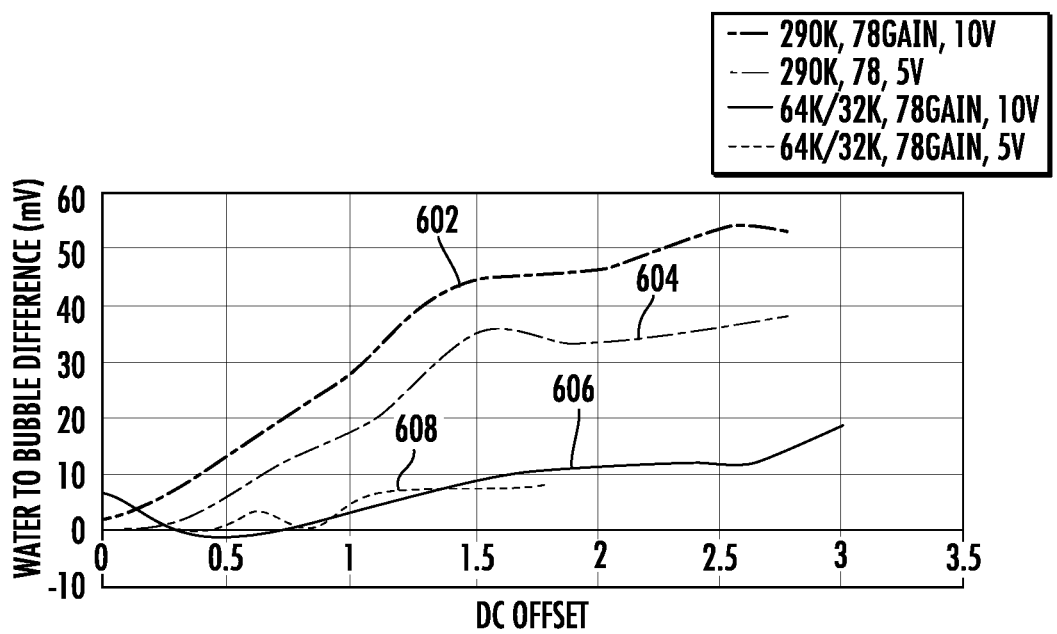
FIGS. 6A and 6B are graphical representations of sensitivity of a force sensor, in accordance with an example embodiment of the present disclosure.
Figure 6B:
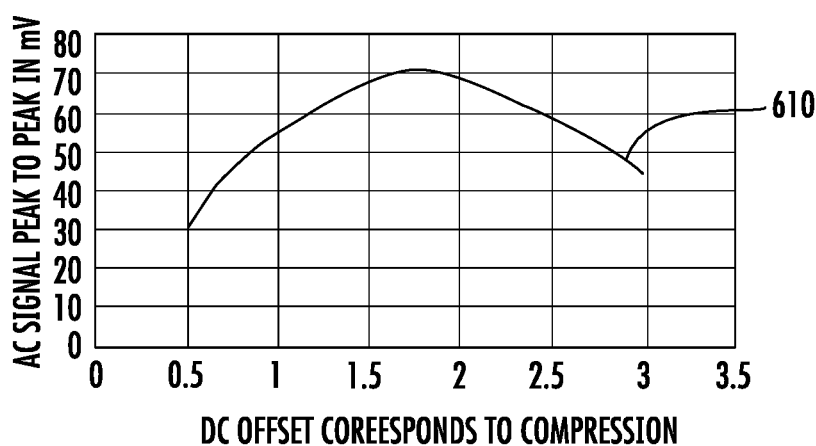

FIGS. 6A and 6B are graphical representations of sensitivity of a force sensor, in accordance with an example embodiment of the present disclosure. The FIGS. 6A and 6B illustrate force sensor sensitivity for air bubble to liquid in the flow tube 106 with increased contact area and force by compressing the flow tube 106, and at different Acoustic Pressure Levels (APL) and working ultrasonic frequency. FIG. 6A has the water to bubble difference plotted on the y-axis and a DC offset on the x-axis. The figure illustrates various signal outputs in response to different conditions of a driving voltage. For instance, a signal 602 is in response to signal parameters of 290 KHz frequency, 78 gain and 10V voltage, a signal 604 is in response to 290 KHz frequency, 78 gain and 5V voltage. A signal 606 is corresponding to 64K/32 KHz, 78 gain and 10V voltage and a signal 608 is corresponding to the signal parameters, 64K/32K, 78 gain and 5V voltage. FIG. 6B illustrates a signal 610 for DC offset and AC peak at frequency of 290 KHz. In an example, the compression of the flow tube 106 is in a range of 10-40% of a diameter of the flow tube 106. In an example, the diameter for the flow tube is in a range of 2.36 millimeters (mm) to 12.7 mm, and an outer diameter is 4.1 mm and inner diameter is 3 mm and with a tube compression of about 20%, the effective gap between the ultrasonic transducer 202 to the force sensor 204 is 3.3 mm. Such a compression provides optimum coupling efficiency and facilitates efficient signal propagation through the flow tube 106.

The operation of the controller 206 is described later in conjunction with FIGS. 7 and 8.

Referring to FIG. 7, in conjunction with FIG. 1, FIG. 2 and FIG. 3, a flowchart 700 illustrating detecting air bubbles and liquid in a flow tube, such as the flow tube 106 is described. FIG. 7 shows the flowchart 700 illustrating operation of the controller, in accordance with the example embodiments described herein.

Turning first to operation 702, a threshold for detecting an air bubble or liquid is determined. In an example, the controller 206 determines the threshold for detecting air bubble and liquid in the flow tube 106 based on an initial condition. The initial condition is for instance, when the flow tube 106 has liquid or air present in the flow tube 106 and the controller 206 determines the threshold based on the predefined percentage of the output signal at the initial condition, referred to as the first output signal. At 704, a change in an output signal is detected. The change in one example is in response to a change in position of the force sensor 204, or change in rate and pressure of the liquid in the flow tube 106 and causes the output signal to change from the first output signal to the second output signal. The controller 206 detects the change based on the amplitude of the AC component when the amplitude of the AC component of the first output signal increases or decreases. In another example, the controller 206 detects the change based on change in the signal level of the DC component of the first output signal when the DC component shifts from the first signal level to the second signal level, also referred to as the new signal. For example, to detect the change in the signal level, the controller measures and records the signal levels of the DC component at multiple time instances and compares the signal level at a time instance 't' with the signal level at an time instance 't-2'. For instance, the controller 206 measures and records the signal level of the first output signal at $30^{th}$ second from the initial condition and compares with the signal level at $28^{th}$ second from the initial condition to detect if the signal levels have changed.

Thereafter, at 706, the change in the output signal is determined to be present for more than a predefined time or a predefined number of transitions. The controller 206 determines a time duration of the second output signal from the instance the first output signal is changed to the second output signal, and a number of transitions in consecutive signal levels of the DC component from the first signal level to the second signal level. In an example, when the second output signal is present for more than the predefined time or the predefined number of transitions, then a new threshold is determined based on the output signal, at 708. In an example, when the second output signal is present for less than the predefined time or the predefined number of transitions, the controller 206 monitors the flow tube 106 for detecting the change in the output signal, at 704.

At 710, the liquid and air bubble are detected based on the new threshold. In an example embodiment, the controller 206 determines the new threshold and detects the air bubbles and liquid in the flow tube 106 based on the new threshold.

Figure 8:
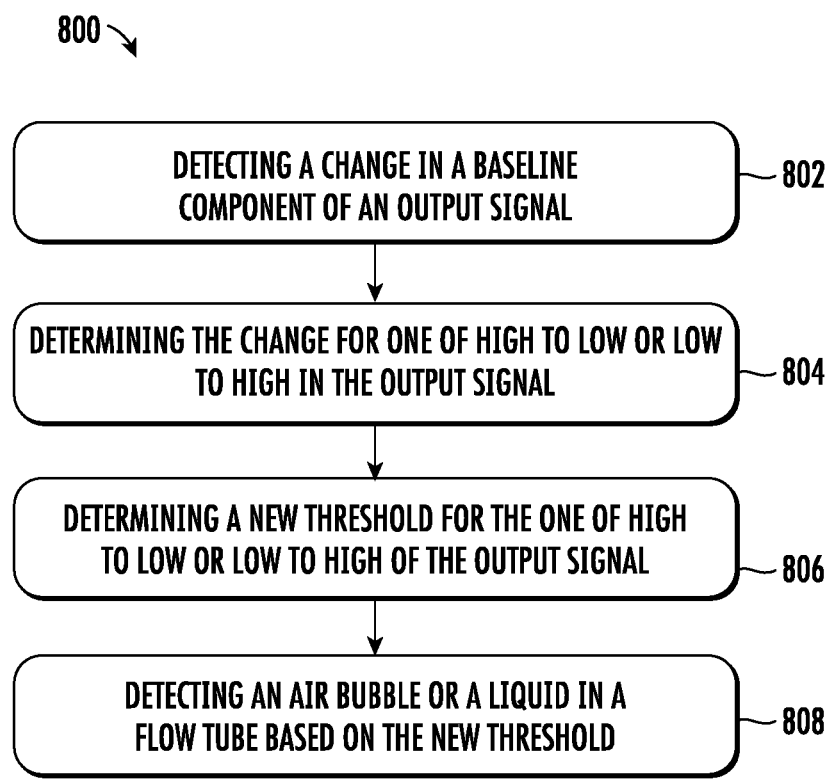
FIG. 8 illustrates an example method for detecting liquid or air bubble in a flow tube based on a new threshold, in accordance with an example embodiment of the present disclosure.

FIG. 8 illustrates an example method 800 for detecting air bubble and liquid in a flow tube, such as the flow tube 106, in accordance with an example embodiment of the present disclosure.

At 802, a change is detected in a baseline component of an output signal. For example, the controller 206 detects the change in the baseline component 404 or the DC component of the output signal of the force sensor 204. At 804, the change is determined to be one of a high to low or low to high for the baseline component. In the change of signal levels from low to high, the first signal level of the first output signal changes to the second signal level of the second output signal and the second signal level is higher than the first signal level. In the change of the signal level from high to low, the second signal level is at a lower level than the first signal level. In an example, the rise of the signal level, from low to high, indicates presence of air bubble and occlusion and a fall in the signal level, from high to low, indicates presence of air bubbles and no occlusion, as shown in FIG. 4C.

At 806, a new threshold is determined for the change of the output signal from one of high to low or low to high of the signal level. In an example, the controller 206 determines the new threshold based on a shift of the base line component when the base line component rises to a higher signal level or falls to a lower signal level. Thereafter, at 808, liquid or air bubble are detected based on the new threshold. In an example, the controller 206 determines the new threshold based on a predefined percentage of the output signal and then detects the liquid or air bubble based on the new threshold.

FIG. 7 illustrates example flowchart and FIG. 8 illustrates example method describing operations performed in accordance with example embodiments of the present disclosure. It will be understood that each block of the flowcharts, and combinations of blocks in the flowcharts, may be implemented by various means, such as devices comprising hardware, firmware, one or more processors, and/or circuitry associated with execution of software comprising one or more computer program instructions. For example, one or more of the procedures described above may be embodied by computer program instructions residing on a non-transitory computer-readable storage memory. In this regard, the computer program instructions which embody the procedures described above may be stored by a memory of an apparatus employing an embodiment of the present disclosure and executed by a processor of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. When executed, the instructions stored in the computer-readable storage memory produce an article of manufacture configured to implement the various functions specified in flowchart blocks. Moreover, execution of a computer or other processing circuitry to perform various functions converts the computer or other processing circuitry into a machine configured to perform an example embodiment of the present disclosure. Accordingly, the operations set forth in the flowcharts define one or more algorithms for configuring a computer or processor, to perform an example embodiment. In some cases, a general-purpose computer may be provided with an instance of the processor which performs algorithms described in one or more flowcharts to transform the general-purpose computer into a machine configured to perform an example embodiment.

Accordingly, the described flowchart blocks support combinations of means for performing the specified functions and combinations of operations for performing the specified functions. It will also be understood that one or more flowchart blocks, and combinations of flowchart blocks, can be implemented by special purpose hardware-based computer systems which perform the specified functions, or combinations of special purpose hardware that execute computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

In one or more example embodiments, the functions described herein may be implemented by special-purpose hardware or a combination of hardware programmed by firmware or other software. In implementations relying on firmware or other software, the functions may be performed as a result of execution of one or more instructions stored on one or more non-transitory computer-readable media and/or one or more non-transitory processor readable media. These instructions may be embodied by one or more processor-executable software modules that reside on the one or more non-transitory computer-readable or processor-readable storage media. Non-transitory computer-readable or processor-readable storage media may in this regard comprise any storage media that may be accessed by a computer or a processor. By way of example but not limitation, such non-transitory computer readable or processor-readable media may comprise Random Access Memory (RAM), Read Only Memory (ROM), Electrically Erasable Programmable Read-Only Memory (EEPROM), FLASH memory, disk storage, magnetic storage devices, or the like. Disk storage, as used herein, comprises compact disc (CD), laser disc, optical disc, digital versatile disc (DVD), floppy disk, and Blu-ray Disc™, or other storage devices that store data magnetically or optically with lasers. Combinations of the above types of media are also included within the scope of the terms non-transitory computer-readable and processor-readable media. Additionally, any combination of instructions stored on the one or more non-transitory processor-readable or computer-readable media may be referred to herein as a computer program product.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments, but not other embodiments.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present disclosure are disclosed herein; however, it is to be understood that the disclosed embodiments are merely exemplary, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

While it is apparent that the illustrative embodiments herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present disclosure.

What is claimed is:

1. A method for detecting an air bubble or liquid in a flow tube of a fluid flow system, the method comprising:
    monitoring a first output signal of a force sensor of the fluid flow system for a change from the first output signal to a second output signal, wherein the change from the first output signal to the second output signal comprises at least one of a change in amplitude of an Alternating Current (AC) component of the first output signal and a change in a signal level of a Direct Current (DC) component of the first output signal;
    detecting the change from the first output signal to the second output signal, wherein the change in the amplitude of the AC component is detected based on an increase or a decrease of the amplitude of the AC component, and the change in the signal level of the DC component is detected based on a shift of the signal level from a first signal level to a second signal level;
    determining one of a time duration of the second output signal of the force sensor from an instance the first output signal is changed to the second output signal, and a number of transitions in consecutive signal levels of the DC component from the first signal level to the second signal level;
    comparing the time duration of the second output signal with a predefined time and the number of transitions with a predefined number of transitions; and
    determining a threshold when one of the time duration of the second output signal exceeds the predefined time, and the number of transitions of the DC component exceeds a predefined number of transitions, wherein the threshold is determined based on a predefined percentage of the second output signal.

2. The method of claim 1, wherein the shift of the DC component from the first signal level to the second signal level comprises one of a change from a low signal level to a high signal level and a change from a high signal level to a low signal level.

3. The method of claim 1, wherein the first output signal is received in response to ultrasonic signals transmitted at a frequency range of 20 Kilo Hertz (KHz) to 1 Mega Hertz (MHz).

4. The method of claim 1, wherein the flow tube is disposed within a channel of the force sensor with a tube compression of 10-40% of a diameter of the flow tube.

5. The method of claim 1 further comprising detecting the air bubble or liquid in the flow tube based on the threshold.

6. The method of claim 1, wherein the predefined percentage is 65% of the second output signal.

7. The method of claim 1, wherein the change from the first output signal to the second output signal is in response to one or more of an uncontrolled sensor position, or movement of the flow tube or change in flow rate or pressure.

8. A fluid flow system comprising:
    a force sensor configured to monitor at least one of an air bubble or an occlusion in a flow tube, the force sensor configured to receive ultrasonic signals from an ultrasonic transducer, the ultrasonic transducer having an emitting face configured to emit the ultrasonic signals, and the emitting face is configured to face the flow tube;
    a controller, electrically coupled with the force sensor, wherein the controller is configured to:
        monitor a first output signal of a force sensor of the fluid flow system for a change from the first output signal to a second output signal, wherein the change from the first output signal to the second output signal comprises at least one of a change in amplitude of an Alternating Current (AC) component of the first output signal and a change in a signal level of a Direct Current (DC) component of the first output signal;
        detect the change from the first output signal to the second output signal, wherein the change in the amplitude of the AC component is detected based on an increase or a decrease of the amplitude of the AC component, and the change in the signal level of the DC component is detected based on a shift of the signal level from a first signal level to a second signal level;
        determine one of a time duration of the second output signal of the force sensor, and a number of transitions in consecutive signal levels of the DC component from the first signal level to the second signal level;
        compare the time duration of the second output signal with a predefined time and the number of transitions with a predefined number of transitions; and
        determine a threshold when one of the time duration of the second output signal exceeds the predefined time, and the number of transitions of the DC component exceeds a predefined number of transitions, wherein the threshold is determined based on a predefined percentage of the second output signal.

9. The fluid flow system of claim 8, wherein the force sensor has a receiving face configured to receive the ultrasonic signals for detecting a change in amplitude of the ultrasonic signals, wherein the ultrasonic signals propagate through the flow tube prior to receiving by the force sensor.

10. The fluid flow system of claim 8, wherein the first output signal is received in response to ultrasonic signals transmitted at a frequency range of 20 Kilo Hertz (KHz) to 1 Mega Hertz (MHz).

11. The fluid flow system of claim 8, wherein the flow tube is disposed within a channel of the force sensor with a tube compression of 10-40% of a diameter of the flow tube.

12. The fluid flow system of claim 8, wherein the controller is configured to detect the air bubble or liquid in the flow tube based on the threshold.

13. The fluid flow system of claim 8, wherein the predefined percentage is 65% of the second output signal.

14. The fluid flow system of claim 8, wherein the change from the first output signal to the second output signal is in response to one or more of an uncontrolled sensor position, or movement of the flow tube or change in flow rate or pressure.

15. The system of claim 8, wherein the controller is configured to detect the shift of the DC component from the first signal level to the second signal level based on one of a change from a low signal level to a high signal level and a change from a high signal level to a low signal level.

16. A non-transitory computer-readable medium storing instructions for detecting an air bubble or liquid in a flow tube of a system, the instructions, when executed, cause the system to:
monitor a first output signal of a force sensor of the system for a change from the first output signal to a second output signal, wherein the change from the first output signal to the second output signal comprises at least one of a change in amplitude of an Alternating Current (AC) component of the first output signal and a change in a signal level of a Direct Current (DC) component of the first output signal;
detect the change from the first output signal to the second output signal, wherein the change in the amplitude of the AC component is detected based on an increase or a decrease of the amplitude of the AC component, and the change in the signal level of the DC component is detected based on a shift of the signal level from a first signal level to a second signal level;
determine one of a time duration of the second output signal of the force sensor, and a number of transitions in consecutive signal levels of the DC component from the first signal level to the second signal level;
compare the time duration of the second output signal with a predefined time and the number of transitions with a predefined number of transitions; and
determine a threshold when one of the time duration of the second output signal exceeds the predefined time, and the number of transitions of the DC component exceeds a predefined number of transitions, wherein the threshold is determined based on a predefined percentage of the second output signal.

17. The non-transitory computer-readable medium of claim 16 further comprising instructions, when executed, cause the system to detect the air bubble or liquid in the flow tube based on the threshold.

18. The non-transitory computer-readable medium of claim 16, wherein the predefined percentage is 65% of the second output signal.

19. The non-transitory computer-readable medium of claim 16, wherein the change from the first output signal to the second output signal is in response to one or more of an uncontrolled sensor position, or movement of the flow tube or change in flow rate or pressure.

20. The non-transitory computer-readable medium of claim 16 further comprising instructions, when executed, cause the system to detect the shift of the DC component from the first signal level to the second signal level based on one of a change from a low signal level to a high signal level and a change from a high signal level to a low signal level.

* * * * *